United States Patent [19]

Costin

[11] Patent Number: 5,160,317
[45] Date of Patent: Nov. 3, 1992

[54] COMPUTER CONTROLLED SMART PHACOEMULSIFICATION METHOD AND APPARATUS

[76] Inventor: John A. Costin, 6841 Cliffside Dr., Vermilion, Ohio 44089

[21] Appl. No.: 635,887

[22] Filed: Jan. 3, 1991

[51] Int. Cl.$^5$ .............................................. A61B 17/70
[52] U.S. Cl. .................. 604/22; 128/24 AA; 606/107
[58] Field of Search ............ 604/22, 118; 128/24 AA; 606/107, 171

[56] References Cited

U.S. PATENT DOCUMENTS

| | | |
|---|---|---|
| 3,601,126 | 8/1971 | Estes et al. . |
| 3,812,855 | 5/1974 | Banko ............................. 128/24 AA |
| 3,812,858 | 5/1974 | Oringer . |
| 3,902,495 | 9/1975 | Weiss et al. ............. 604/22 |
| 3,930,505 | 1/1976 | Wallach . |
| 3,964,487 | 6/1976 | Judson . |
| 4,024,467 | 5/1977 | Andrews et al. . |
| 4,024,866 | 5/1977 | Wallach . |
| 4,114,623 | 9/1978 | Meinke et al. . |
| 4,126,137 | 11/1978 | Archibald . |
| 4,168,707 | 9/1979 | Douvas et al. ..................... 606/107 |
| 4,184,510 | 1/1980 | Murry et al. ....................... 604/22 |
| 4,223,676 | 9/1980 | Wuchinich et al. . |
| 4,496,342 | 1/1985 | Banko . |
| 4,508,532 | 4/1985 | Drews et al. ......................... 604/22 |
| 4,590,935 | 5/1986 | Ranalli ................................. 604/22 |
| 4,651,280 | 3/1987 | Chang et al. . |
| 4,658,819 | 4/1987 | Harris et al. . |
| 4,705,500 | 11/1987 | Reimels et al. ...................... 604/22 |
| 4,712,544 | 12/1987 | Ensslin . |
| 4,739,759 | 4/1988 | Rexroth et al. . |
| 4,750,488 | 6/1988 | Wuchinich et al. . |
| 4,770,654 | 9/1988 | Rogers et al. . |
| 4,793,345 | 12/1988 | Lehmer . |
| 4,969,885 | 11/1990 | Farin . |
| 5,026,387 | 6/1991 | Thomas ............................. 604/22 |

FOREIGN PATENT DOCUMENTS

| | | | |
|---|---|---|---|
| 0359217 | 3/1990 | European Pat. Off. ............. 604/22 |
| 8705793 | 10/1987 | World Int. Prop. O. ............. 604/22 |

*Primary Examiner*—Stephen C. Pellegrino
*Assistant Examiner*—Michael Rafa
*Attorney, Agent, or Firm*—Cushman, Darby & Cushman

[57] ABSTRACT

A method and apparatus for operating on the human eye detects changes in load on the transducer and controls aspiration based on the load changes. A change from a lower load to a higher load indicates that harder tissue is being encountered and accordingly causes aspiration amount to increase. Conversely, a change from a higher load to a lower load indicates that aspiration amount should be quickly decreased since the tissue which is being encountered is softer.

21 Claims, 6 Drawing Sheets

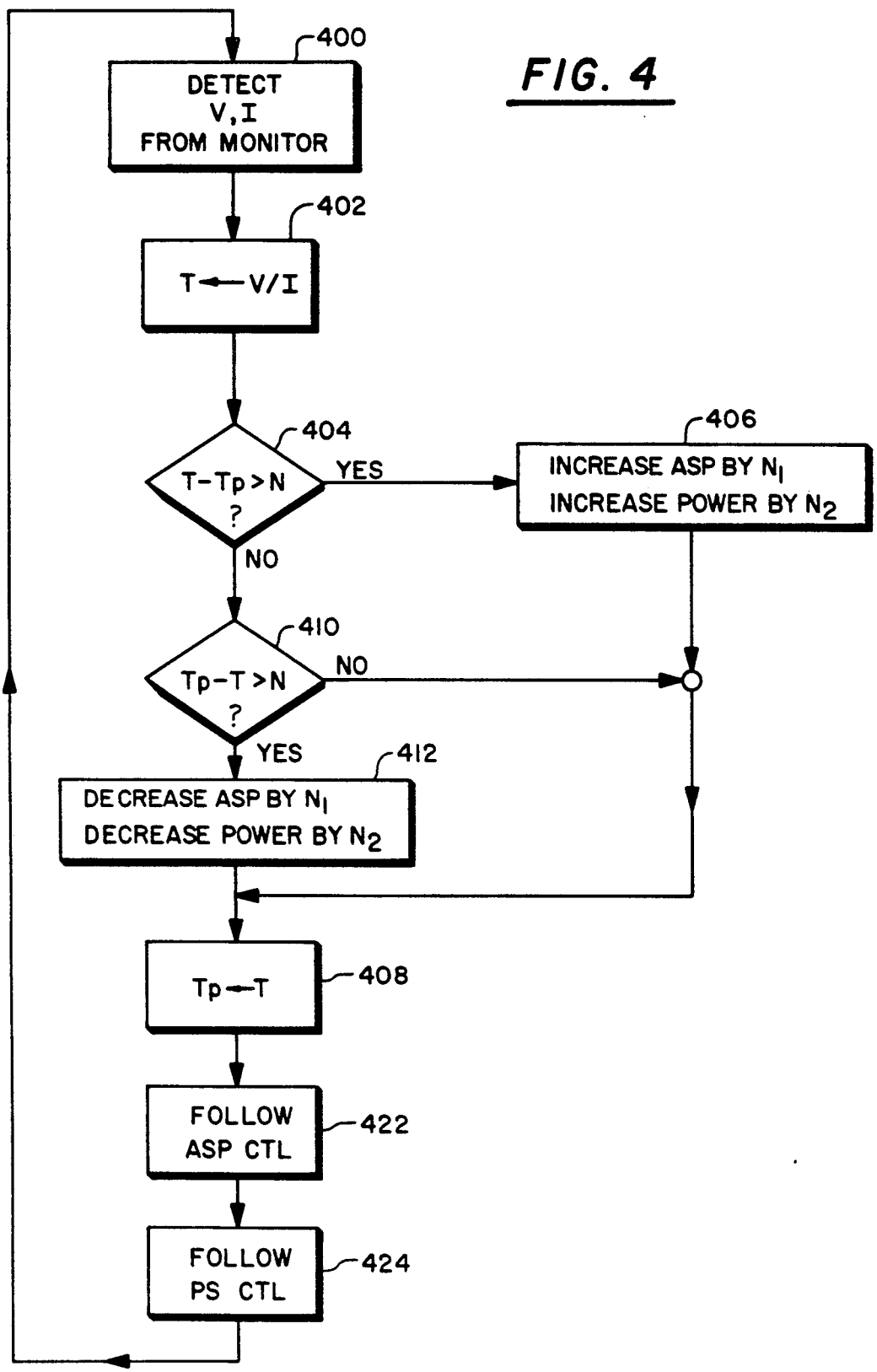

COMPUTER CONTROLLED SMART PHACOEMULSIFICATION METHOD AND APPARATUS

FIELD OF THE INVENTION

The present invention relates to a computer controlled "smart" phacoemulsification apparatus, and more specifically to one which controls power delivery to the needle of the transducer and also controls an amount of aspiration based on a load on the tip of the transducer.

BACKGROUND AND SUMMARY OF THE INVENTION

Eye surgery is a complicated and delicate process. One common eye surgery is cataract extraction. There are currently several methods of acceptable cataract extraction, including phacoemulsification. Phacoemulsification is not in itself new, but as currently done has many problems.

Phacoemulsification involves the generation of an ultrasonic signal which is a series of cyclical mechanical vibrations in a frequency range beyond that detectable by normal human hearing. The ultrasonic signal is generated by a transducer that is driven by an electrical signal in a frequency range between 20 and 100 kilohertz in equipment presently available for this application. Typically the transducer mechanism includes either piezoelectric or magnetostrictive elements.

The energy resulting from the ultrasonic signal is coupled to the human lens by a needle attached to the transducer. Typically the needle is made from an inert alloy of titanium or stainless steel. Once coupled to the human lens, the ultrasonic energy fragments and emulsifies the cataract. Once this nuclear material is fragmented, however, it must be removed from the eye. In order to do this, the ultrasonic needle is hollow, and an aspiration system is connected to the hollow area in order to remove the fragmented particles. A balanced salt solution is also injected in order to maintain the stability or pressure, and this infusion occurs around the vibrating titanium needle through a sleeve.

An example of such a phacoemulsification unit is shown in U.S. Pat. No. 4,223,676, the disclosure of which is hereby incorporated by reference. Current phacoemulsification surgery allows the surgeon to choose either a fixed phaco mode in which the power setting to the transducer is fixed, or a linear mode in which the phaco power can be changed by the power peddle. In the fixed mode, the phaco unit is either on or off depending on whether the peddle is depressed or not. The value of power setting is preset. In the linear mode, the further depression of the peddle varies the amount of power to the transducer and thereby the ultrasonic energy. The aspiration during this operation is preset. A third mode of phacoemulsification which has been recently introduced keeps the phaco power fixed and varies the aspiration depending on the foot peddle.

The inventor of the present invention has recognized a problem which exists in these prior operations. In order to fully understand this, one must consider the structure of the lens of the human eye. FIG. 1 shows diagrammatically a human lens which has an outer, fine, transparent tissue or capsule shown as layer 100. Interior to this is a soft material known as the cortex 102, which surrounds the transition layers 104. The nucleus of the lens is a hard, compressed lens material shown as 106. The inventor of the present invention has first noted that in these soft outer cortex layers, little aspiration is required, but more aspiration is required in the harder transitional layers and even more in the hardest nucleus layer. However, posterior to the hardest nucleus layer is a less hard transitional layer followed by a soft cortex. A majority of the complications during eye surgery are caused not by the amount of emulsification, but by over aspiration causing a "punch through" through the posterior lens capsule.

Eye surgery involves forming an opening in the front of the capsule, and locating the phaco needle first into the soft cortex. At this time the needle will experience a minimal load in the soft cortex. As the needle goes further into the nucleus which is progressively harder, the mechanical load increases. After reaching through the nucleus, the process reverses, and the mechanical load will quickly decrease. It is at this point that the inventor of the present invention has found that the control of aspiration becomes critical. Over-aspiration at this time can cause the posterior capsule to be ruptured. However, determination of the relative hardness of these layers has previously been left to the observation skills and manual skills of the surgeon. However, the surgeon has many other things on his mind and also simply may not be able to react fast enough in order to properly change the aspiration amount.

The inventor of the present invention has recognized that a hard nucleus consumes more energy than a soft nucleus, thereby changing the impedance introduced to the ultrasonic tip. According to the present invention, this difference is fed back to a microprocessor in order to modify the aspiration system dependent on the hardness of the material being operated upon. This reduces the problem of "punch through" because it allows automatic checking of the hardness of the material and automatic adjustment of the aspiration delivery in a way which is faster than could ever be done using human reflexes. Such a system has never been described in the prior art.

Many attempts have been made in the prior art in order to attempt to automate operation processes. U.S. Pat. No. 4,223,676 is one such attempt and defines one type of ultrasonic aspirator of the type previously described above. Column 8 of this patent recognizes that frequency fluctuates during the course of an operation, and in order to attempt to maintain the amount of power delivery as constant, this patent teaches monitoring actual and expected parameters of the system. The difference between these two parameters is fed back in a feedback loop to control the stroke level of the vibrator. Therefore, while the power of the system is controlled, there is no teaching of controlling the amount of aspiration, and as such the problem of "punch through" would still remain in this system.

Similarly, U.S. Pat. No. 3,964,487 teaches a structure which monitors the impedance of the electric cutting apparatus, and feeds back this impedance to determine the amount of power to be provided. This device does not teach controlling the amount of aspiration, and therefore would not alleviate the problem of "punch through".

Similarly, U.S. Pat. No. 4,126,137 teaches sensing of the impedance of the tissues to set the amount of drive to an electro-surgical unit.

U.S. Pat. No. 4,024,866 relates to a device which teaches controlling the amount of suction in a suction conduit for eye surgery. Column 7, lines 24 + + teach that an upper limit is placed on the amount of suction to prevent an excessive amount of suction. While this might provide an upper limit, it does not help the user to obtain better control and better feedback of the system.

BRIEF DESCRIPTION OF THE DRAWINGS

These and other aspects of the invention will now be described in detail with reference to the accompanying drawings in which:

FIG. 4 shows a flow chart of operation of this first embodiment;

DESCRIPTION OF THE PREFERRED EMBODIMENTS

Figure 1:
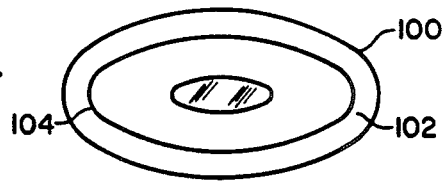
FIG. 1 shows a schematic view of the human eye.
Figure 2:
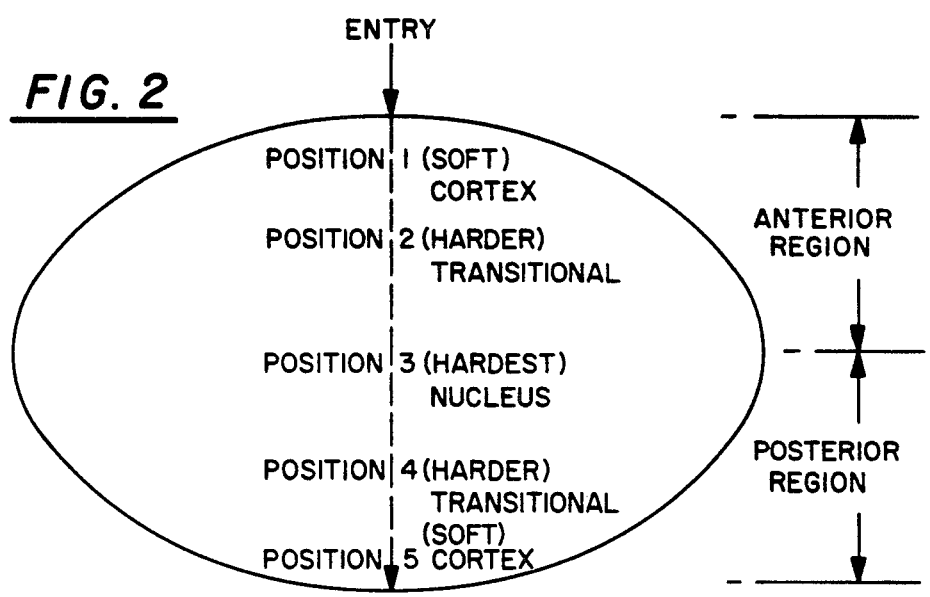
FIG. 2 shows a representative amount of aspiration required in a traversal through the eye.
Figure 2A:
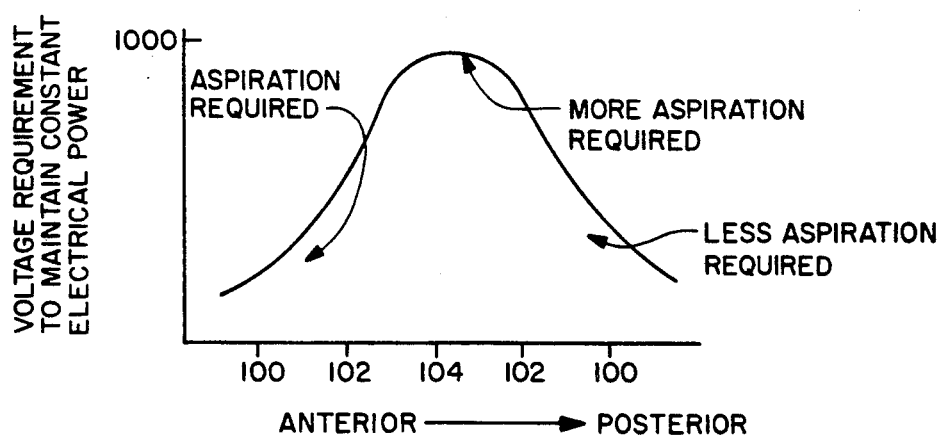
Figure 3:
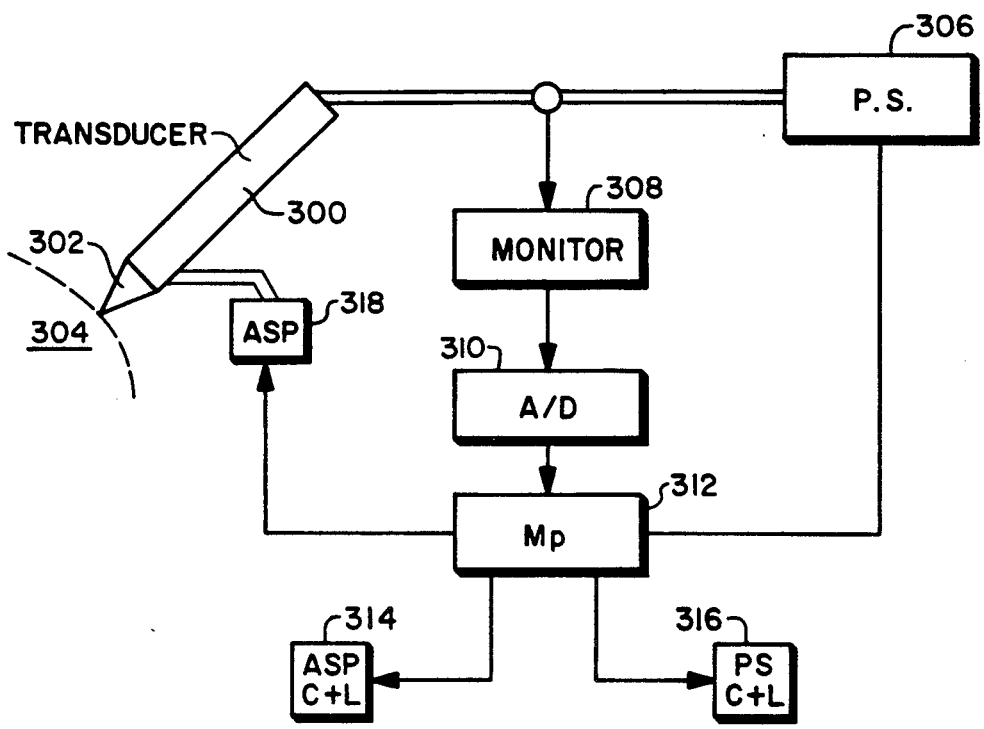
FIG. 3 shows a blocked diagram representation of a first embodiment of the present invention.

A presently preferred embodiment will now be described in detail with respect to the accompanying drawings. FIG. 3 shows a first embodiment of the invention. Transducer 300 is shown attached to needle 302 which is adapted to come into contact with a lens 304 of the human eye. The power supplied by power supply 306 to the transducer 300, and at the same time the voltage and current is monitored by monitor 308. Monitor 308 monitors the voltage and current, and produces analog signals which are converted by analog to digital converter into digital signals, and are input to microprocessor 312. Microprocessor 312 can be any commercially available type. An aspiration control 314 is also input to microprocessor as is a power supply control 316. These devices can be either dial-type potentiometers or the usual surgeon's foot peddle, and produce a command signal indicative of the amount of aspiration and power respectively desired. Microprocessor 312 produces analog signals which control the aspiration unit 318 in the power supply 306.

The microprocessor operates according to the flowchart of FIG. 4, and accordingly controls the aspiration 318 and power supply 306 based on this flowchart. Step 400 detects voltage and current from monitor 308, and takes a ratio between this voltage and current at step 402. This ratio is stored in a variable T. This variable measures a linkage of the instantaneous aspiration with varying phaco needle load and can be implemented in at least two different forms.

First we must recognize that a positive correlation has been established between the electrical power consumed by an ultrasonic transducer and the mechanical motion of a needle attached to it. One way, therefore, would be tracking impedance (voltage in/current in).

$$\text{impedance} = \text{voltage} \div \frac{1}{\text{current}}$$

-continued $$Z = V \times \left(\frac{1}{I}\right)$$

A multiplier circuit could be used to accomplish this. Changes in the load would allow the control system to compensate in a variety of ways be affecting both electrical power and aspiration levels. Alternately, the difference between commanded power levels and actual power consumed could also be measured directly with only one multiplier circuit i.e.

power = voltage × current $$p = V \times I$$

Both power levels (V*I) and V/I are referred to generically herein as "Impedance".

Step 404 makes a test by taking the current variable T and subtracting a previous value of the variable T called herein $T_p$, and then determining if $T - T_p$ is greater than a value N. If it is, this means that the impedance of the tissue currently, is greater than the impedance at a previous time and that the current tissue is therefore harder than the previous tissue. Therefore, if the test at step 404 is positive, step 406 is executed, which increases the aspiration rate by $N_1$ and increases the power by $N_2$. The flow then passes to step 408 in which the current value of T is stored in the location $T_p$ in preparation for a following cycle.

If the result at step 404 is negative and the difference between T and $T_p$ is not greater than N, a second test is made at step 410. Step 410 determines if the value of $T_p$ is greater than the current T by the amount N. If not, flow again passes to step 408. Therefore, if the difference between T and $T_p$ is less than the value N, no modification of aspiration or power takes place.

If $T_p$ is greater than T by more than the amount N, this indicates that the impedance at the previous time is greater than the impedance at the current time. Accordingly, the aspiration is decreased by the value $N_1$ and the power is decreased by the value $N_2$ at step 412.

The following steps, 420 and 422, follow the lead of the aspiration controller 314 and power supply controller 316 respectively. If these values are increased, the power to the appropriate component is also increased, according to a previously designated alogrithm.

The specific structure and method steps enabling control of both power and aspiration according to the impedance encountered by the transducer is in no way taught or suggested by the prior art and is totally novel thereover.

Figure 5:
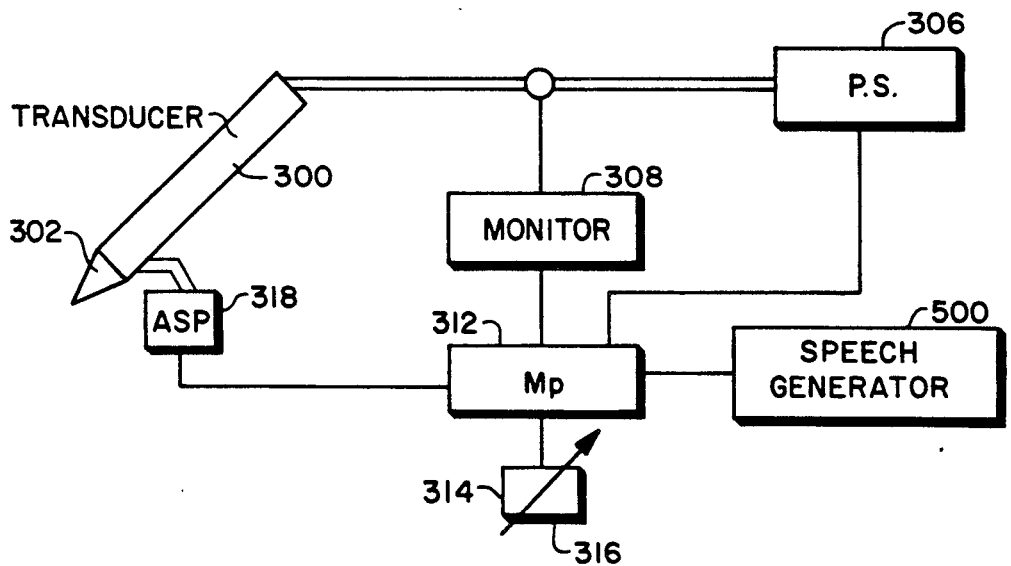
FIG. 5 shows a blocked diagram representation of a second embodiment of the present invention which uses a speech enuniciator to aid the surgeon with his operation.

A second embodiment of the invention is shown in FIG. 5 where like numerals represent like elements. This second embodiment of the invention uses, in addition to the above monitoring system, a speech generating module 500 which enables talking to the surgeon while he is operating.

Current phaco units have visual displays and audio feedback. The visual displays may show the mode in which the machine is engaged, for instance, foot peddle position and irrigation only, irrigation and aspiration, etc. The audio feedback may be different sounds in different units that indicate a transition, such as a beep or a click.

However, all of these sounds may be very confusing to a surgeon who is first learning to do the phaco procedure. Such a surgeon has many other things to concentrate on and often times finds extra confusion in where on the foot peddle they are and precisely what is happening. The second embodiment of the present invention enables the use of commercially available speech generating equipment to help avoid this confusion.

Figure 6:
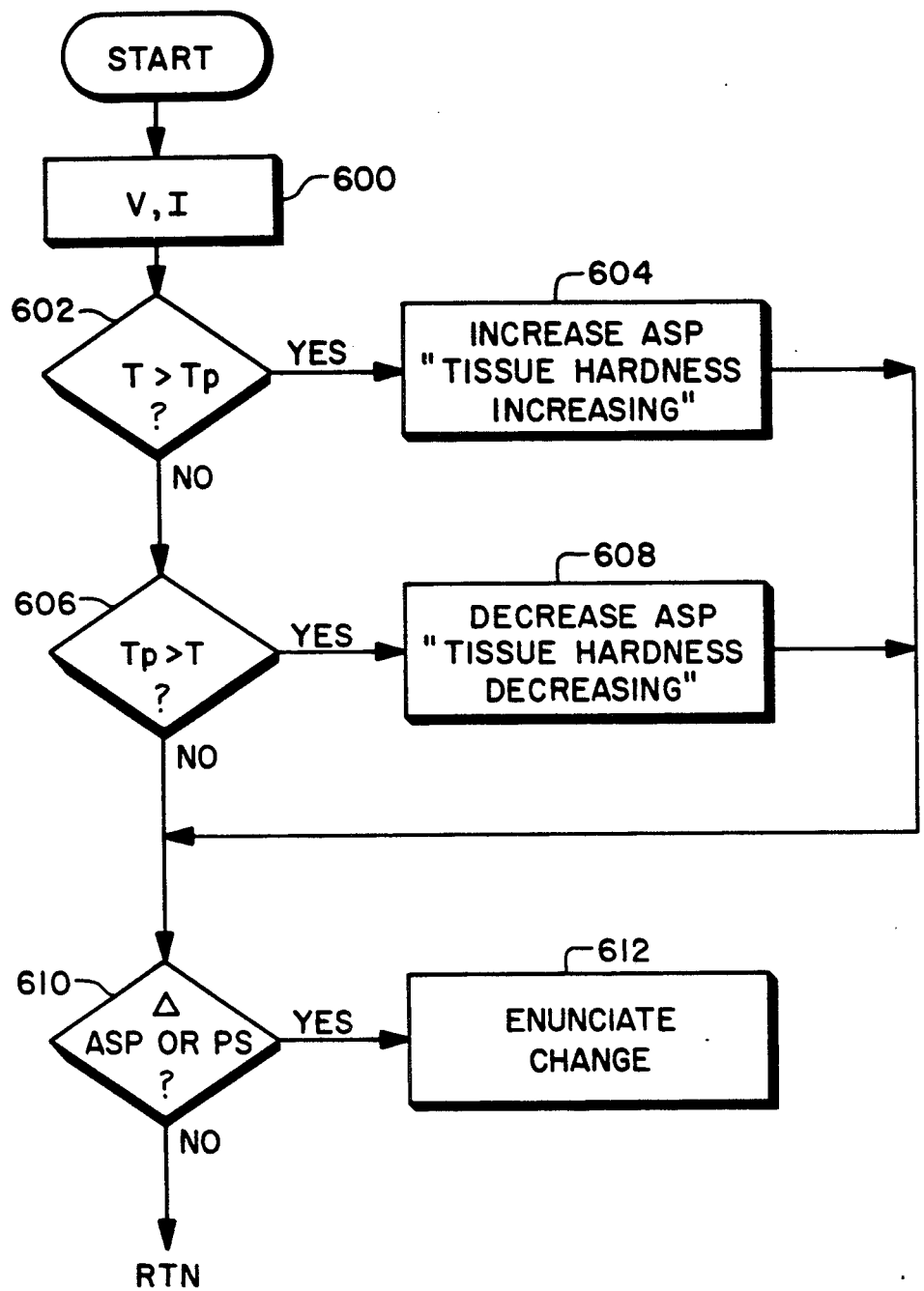
FIG. 6 shows a flow chart of operation of the second embodiment.

According to this embodiment of this invention, the speech generating unit 500 can be a commercially available speech generating chip and audio equipment, or it can be, for instance, a series of tapes or recorded tracks which can be accessed by an appropriate processor. Such devices are well known in the art and will not be discussed further. This device operates according to the flowchart of FIG. 6. FIG. 6 has many common elements with FIG. 4, and starts out in step 600 with detecting V and I and the value T. Step 602 determines if T is greater than $T_p$ by the value N, and if so, increases aspiration and power and also energizes speech generator 500 to say "tissue hardness increasing". Step 606 determines if $T_p$ is greater than T by a certain amount, and if yes, executes steps 608 by decreasing aspiration and enunciating that the tissue hardness is decreasing. Step 610 determines if there has been a change in aspiration or power supply control and if so, enunciates this change. For instance, a foot peddle in position one might be enunciated to say "irrigation" and in position 2 would be enunciated as "irrigation and aspiration". The enunciator might also say at step 612 "phaco fixed at 10%" or "phaco increased to 15%".

This would enable the surgeon to maintain his concentration during this very difficult time of the operation.

Figure 7:
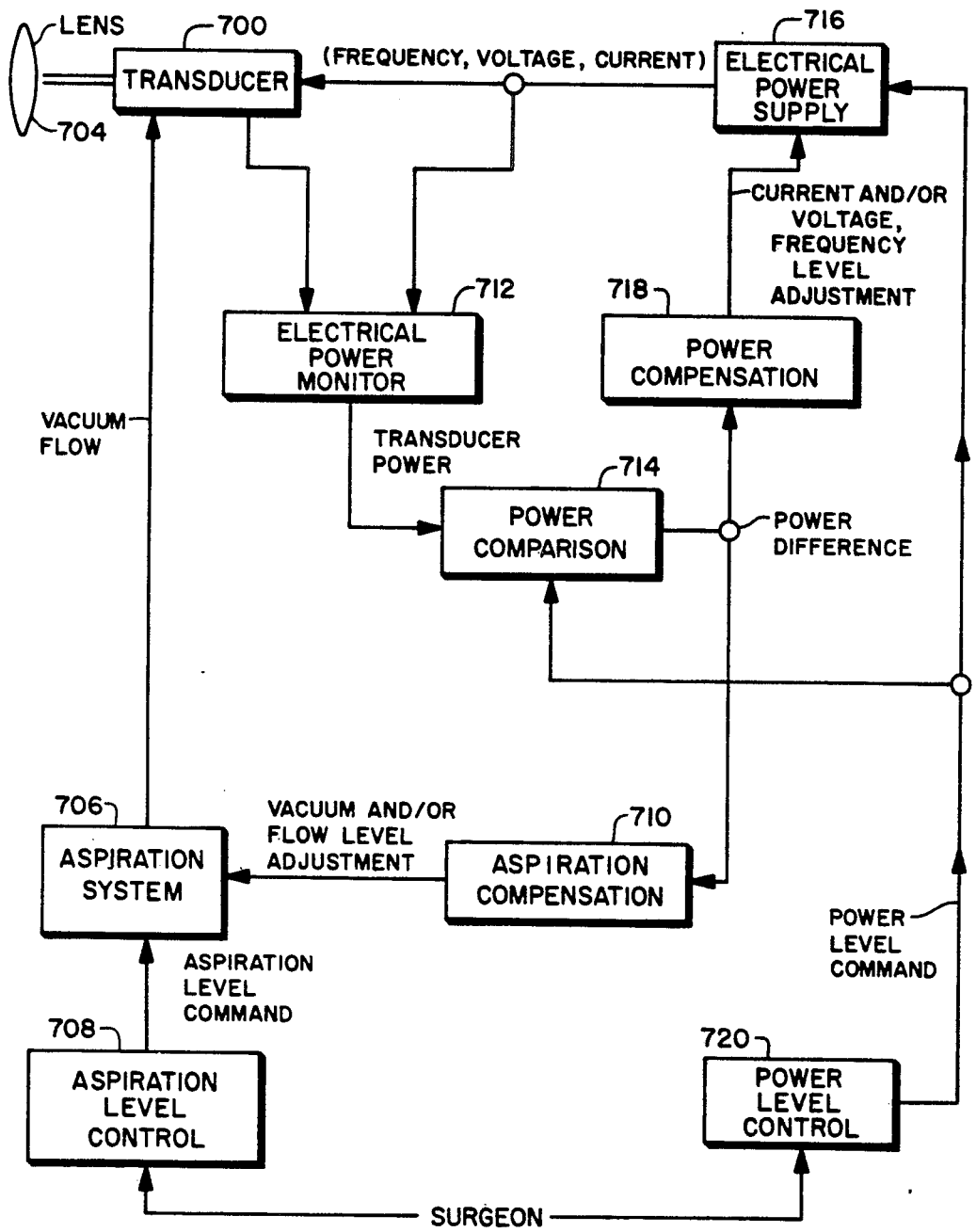
FIG. 7 shows a structure of the third embodiment of the present invention.
Figure 8:
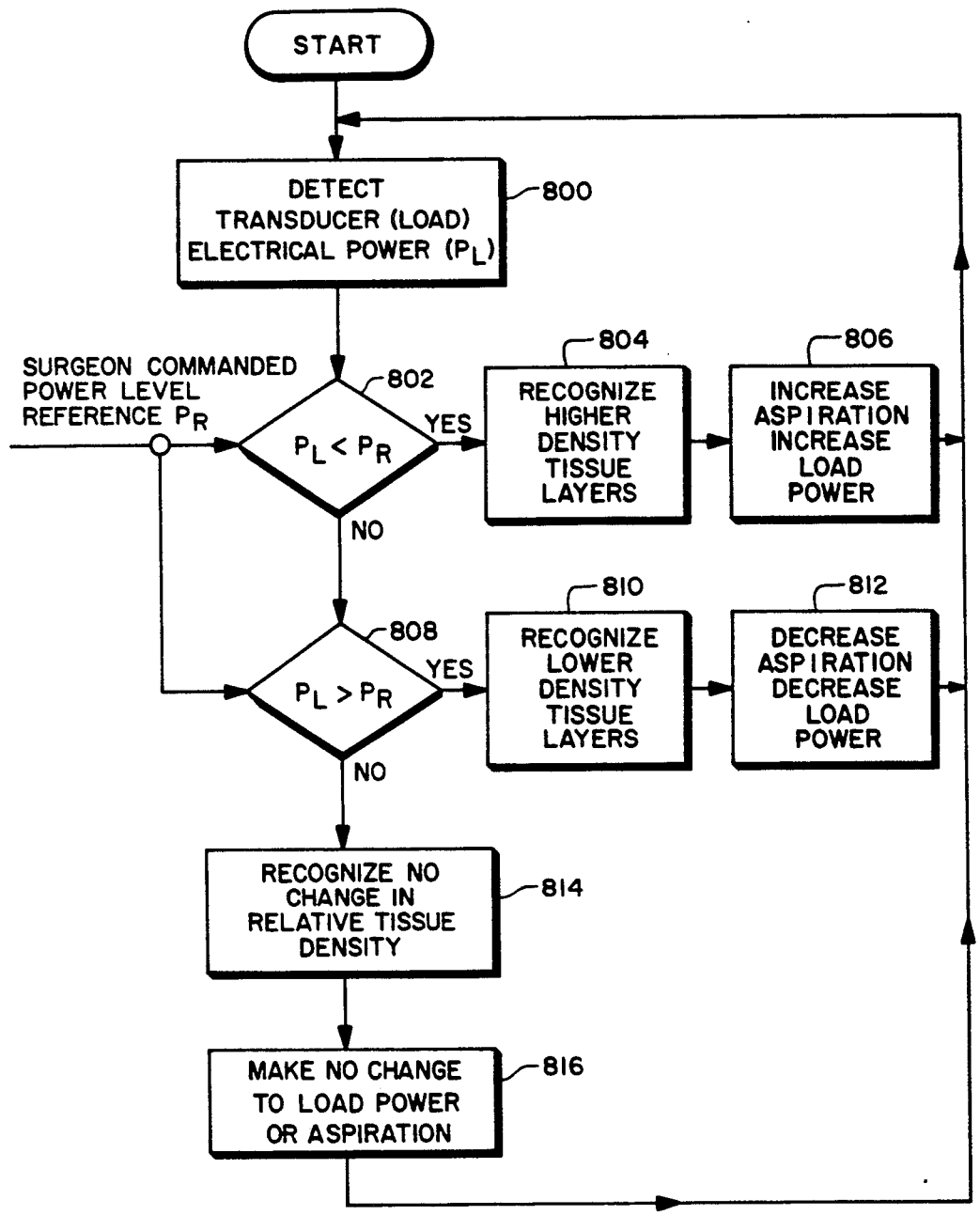
FIG. 8 shows a flow chart of this operation.

A third embodiment for the smart phacoemulsification system would be described by FIG. 7 and the flow chart in FIG. 8. The key to the successful operation of this system is twofold. First, the surgeon has independent control over both transducer load power and aspiration reference levels. Secondly, the automatic control system power monitor and both power and aspiration compensation mechanisms provide measured improvements in the surgeon's control of the transducer by linking the aspiration system compensation with the drive signal for the power compensation.

Electrical power supply 716 provides voltage and current at some frequency to transducer 700. Needle 702 makes contact with the human lens 704 and experiences a varying mechanical load dependent on the density of tissue layers. The surgeon establishes reference power and aspiration levels via independent means 720 power level control and 708 aspiration level control. Electrical power supply 716 responds to power level commands and to power compensation commands (voltage, current or possibly frequency adjustments). These commands originate from modules 720 and 718 respectively. The varying mechanical load on needle 702 is reflected via transducer 700 as a changing electrical load consuming different amounts of electrical power from the reference power level command.

Power monitor 712 senses load voltage and current from transducer 700 and computes electrical power. Transducer power consumption is fed to power comparison module 714 which outputs a difference between actual transducer power and the independent reference level from the power command. Power compensation module 718 responds by appropriate electrical adjustments to power supply 716 such that transducer power consumption will track the independent command from the surgeon.

The unique safety improvement feature of this system results from the application of the power compensation drive signal (power comparison output) to the aspiration compensation module 710. The output of the aspiration compensation module 710 will be an adjustment to vacuum, or flow or both, depending on the type of aspiration system.

As with power, the surgeon has independent input control via 708 to press the output (vacuum and flow) of aspiration system 706. The entire system follows a straightforward control scheme as described by the flowchart FIG. 8. Note that any changes induced by the compensation modules will force the load power to track the independent power level command from the surgeon. Also, the aspiration changes will be added to the independent aspiration level commands from the surgeon. In this way, the surgeon maintains control over the procedure.

Description of FIG. 8 flowchart: The FIG. 8 flowchart shows detecting the transducer load and electrical power at step 800, followed by determinations at step 802 and 808 as to whether the power is less than or greater than a reference $P_r$. If the current electrical power $P_l$ is less than $P_r$, higher density tissue layers are recognized at step 804, followed by the aspiration increase load power at step 806. If the load $P_l$ is recognized as greater than $P_r$ at step 808, lower density tissue layers are recognized at step 810, followed by a decrease in the aspiration and step 812. Step 814 determines if no change in relative tissue density is recognized, followed by no change in load power or aspiration at step 816.

Although only a few embodiments have been described in detail above, those having ordinary skill in the art will understand that many modifications are possible in this embodiment without detracting from the advantages of the invention. All such modifications are intended to be encompassed within the following application.

What is claimed is:

1. A control system for an ultrasonic transducer which includes an aspiration port for operating on a human eye, comprising:
   means for monitoring changes in a load encountered by the ultrasonic transducer; and
   means for controlling an amount of aspiration based on said load changes, and for changing an amount of aspiration to automatically increase when a load on the transducer increases, and changing said amount of aspiration to automatically decrease when the load decreases.

2. A control system as in claim 1 wherein said monitoring means monitors an electrical impedance of the ultrasonic transducer.

3. A control system as in claim 2 wherein said impedance monitoring means includes means for multiplying current used by said ultrasonic transducer by voltage used by ultrasonic transducer to obtain a value indicative of said impedance.

4. A control system as in claim 1 wherein said aspiration controlling means increases said aspiration amount only when said load change is greater than a predetermined amount, and decreases said aspiration amount only when said load change is less than a predetermined negative amount.

5. A control system as in claim 4 wherein said aspiration controlling means also increases a power applied to said ultrasonic transducer when it increases aspiration and also decreases power to said ultrasonic transducer when it decreases aspiration.

6. A control system as in claim 1 wherein said aspiration controlling means also increases a power applied to said ultrasonic transducer when it increases aspiration and also decreases power to said ultrasonic transducer when it decreases aspiration.

7. A control system as in claim 1 further comprising a speech generating module for producing speech indicative of messages whenever said load changes.

8. A method of controlling an operation in a human eye comprising the steps of:
   operating a transducer to conduct said operation;
   detecting a load presented to the transducer;
   determining a relation between a load presented to the transducer with respect to a previous load presented to the transducer;
   automatically increasing an amount of aspiration if said load is greater than said previous load; and
   automatically decreasing said amount of aspiration if said load is less than said previous load.

9. A method as in claim 8 wherein said detecting a load step monitors an electrical impedance of said transducer.

10. A method as in claim 8 wherein said detecting step includes detecting a voltage to said transducer, detecting a current to said transducer, and multiplying said voltage by said current to determine a value indicative of said electrical impedance.

11. A method as in claim 8 wherein said amount of aspiration is increased only when said load change is greater than a predetermined amount, and said amount of aspiration is decreased only when said load change is less than a predetermined negative amount.

12. A method as in claim 11 comprising the further steps of increasing power to said ultrasonic transducer when it increases aspiration and also decreases power when it decreases aspiration.

13. A method as in claim 8 comprising the further steps of increasing power to said ultrasonic transducer when it increases aspiration and also decreases power when it decreases aspiration.

14. A method as in claim 8 comprising the further steps of using a speech generator to announce whenever said increasing or decreasing steps are performed.

15. An apparatus for enabling operations on a human eye comprising:

means for applying ultrasound to the eye, including aspiration means for removing particles, produced by said ultrasound, from the human eye;
means for monitoring conditions of said ultrasound applying means, and said aspiration means;
means for producing a voice sound indicative of changes in at least one of said ultrasound applying means and said aspiration means;
means for monitoring changes in a load encountered by said ultrasound applying means, said voice sound produced by said voice-producing means being indicative of said changes in load; and
means for controlling an amount of aspiration produced by said aspiration means based on said changes in load.

16. An apparatus as in claim 15 wherein said monitoring means includes means for detecting a voltage applied to said ultrasound means, means for detecting a current applied to said ultrasound means, and means for multiplying said voltage by said current to obtain a value indicative of said load.

17. An apparatus for operating on a human eye comprising:
   a operating needle of the type for surgically operating on an area of said eye;
   means for aspirating said area during said operation on said eye;
   means for determining whether a hardness of said area of said eye is changing; and
   means for automatically changing an amount of aspiration produced by said aspirating means when said hardness changes by more than a predetermined amount.

18. An apparatus as in claim 17, wherein said operating means is an ultrasonic transducer.

19. An apparatus as in claim 18 wherein said hardness detecting means includes means for determining an electrical impedance of said ultrasonic transducer.

20. An apparatus as in claim 17 further comprising speech generating means for providing speech indicative of said hardness changing.

21. A method of operating on an area of the human eye comprising the steps of:
   determining a hardness of said area of said human eye;
   determining if said hardness has changed with respect to a previous hardness detected at a previous time;
   aspirating said area of said human eye; and
   automatically changing an amount of said aspiration when said hardness changes by more than a predetermined amount.

* * * * *